(12) United States Patent
Bak et al.

(10) Patent No.: US 12,133,835 B2
(45) Date of Patent: Nov. 5, 2024

(54) EXTRACT FROM PLANT STEEPED IN ALLULOSE AND PREPARATION METHOD THEREFOR

(71) Applicant: CJ CHEILJEDANG CORPORATION, Seoul (KR)

(72) Inventors: Youn Kyung Bak, Suwon-si (KR); Su Jeoung Kim, Suwon-si (KR); Jung Gyu Park, Incheon (KR); Sung Bae Byun, Sejong (KR); Seung Won Park, Yongin-si (KR); Dong Chul Jung, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 322 days.

(21) Appl. No.: 16/338,492

(22) PCT Filed: Jun. 23, 2017

(86) PCT No.: PCT/KR2017/006629
§ 371 (c)(1),
(2) Date: Apr. 1, 2019

(87) PCT Pub. No.: WO2018/070637
PCT Pub. Date: Apr. 19, 2018

(65) Prior Publication Data
US 2019/0247323 A1    Aug. 15, 2019

(30) Foreign Application Priority Data

Oct. 10, 2016    (KR) .................. 10-2016-0130695

(51) Int. Cl.
| | | |
|---|---|---|
| A61K 31/047 | (2006.01) | |
| A23L 21/12 | (2016.01) | |
| A23L 29/30 | (2016.01) | |
| A61K 36/736 | (2006.01) | |
| A61K 36/752 | (2006.01) | |
| A61P 39/06 | (2006.01) | |

(52) U.S. Cl.
CPC ............ *A61K 31/047* (2013.01); *A23L 21/12* (2016.08); *A23L 29/30* (2016.08); *A61K 36/736* (2013.01); *A61K 36/752* (2013.01); *A61P 39/06* (2018.01)

(58) Field of Classification Search
CPC .. A61K 31/047; A61K 36/736; A61K 36/752; A61K 2300/00; A23L 29/30; A23L 29/32; A23V 2002/00; A23V 2200/132
See application file for complete search history.

(56) References Cited

U.S. PATENT DOCUMENTS

| | | | |
|---|---|---|---|
| 9,109,266 B2 | 8/2015 | Takamine et al. | |
| 9,125,409 B2 * | 9/2015 | Ohara | ........... A01N 43/16 |
| 9,259,022 B2 | 2/2016 | Woodyer et al. | |
| 10,729,632 B2 | 8/2020 | Fletcher | |
| 2009/0304891 A1 | 12/2009 | Fujihara et al. | |
| 2012/0004099 A1 * | 1/2012 | Kurahashi | ............. A01N 43/78 |
| | | | 504/100 |
| 2012/0070534 A1 | 3/2012 | Suzuki | |
| 2014/0271746 A1 | 9/2014 | Woodyer | |
| 2014/0271747 A1 | 9/2014 | Lindner et al. | |
| 2014/0349950 A1 | 11/2014 | Kim et al. | |
| 2014/0370171 A1 | 12/2014 | Takaoka | |
| 2015/0110940 A1 | 4/2015 | Lee | |
| 2016/0021917 A1 | 1/2016 | Woodyer | |
| 2016/0050958 A1 | 2/2016 | Woodyer et al. | |
| 2016/0198751 A1 | 7/2016 | Fletcher | |
| 2016/0302463 A1 | 10/2016 | Woodyer | |
| 2016/0331014 A1 | 11/2016 | Perera | |
| 2016/0346305 A1 | 12/2016 | Kim et al. | |
| 2017/0079313 A1 | 3/2017 | Woodyer | |
| 2018/0049454 A1 | 2/2018 | Fujihara et al. | |
| 2018/0049458 A1 | 2/2018 | Woodyer | |
| 2018/0243325 A1 | 8/2018 | Choi | |
| 2019/0218488 A1 | 7/2019 | Choi | |
| 2019/0239539 A1 | 8/2019 | Shim | |
| 2019/0246673 A1 | 8/2019 | Park | |
| 2019/0328014 A1 | 10/2019 | Boit et al. | |
| 2021/0401011 A1 | 12/2021 | Choi | |

FOREIGN PATENT DOCUMENTS

| | | |
|---|---|---|
| CL | 2016000258 A1 | 9/2016 |
| CL | 2016002955 A1 | 5/2017 |
| CL | 2017002161 A1 | 4/2018 |
| CL | 2018000523 A1 | 2/2019 |
| CL | 2019000851 A1 | 6/2019 |
| CL | 2019000872 A1 | 6/2019 |
| CL | 2019000875 A1 | 6/2019 |
| CN | 104207137 B | 1/2016 |
| CN | 105792671 A | 7/2016 |
| CN | 103997913 B | 9/2016 |
| CN | 109661181 A | 4/2019 |

(Continued)

OTHER PUBLICATIONS

Yamada et al. Environ. Control Biol., 52 (3), 155-160. (Year: 2014).*
Imahori et al. Postharvest Biology and Technology 49 (2008) 54-60. (Year: 2008).*
Tameike et al. "Chapter IX—Fruits" from Useful Plants of Japan Described and Illustrated. Agricultural Society of Japan: Tokyo. p. 46 (entries 175 and 177). (Year: 1895).*
Dan Charles (https://www.npr.org/sections/thesalt/2015/08/25/434597445/in-the-hunt-for-the-perfect-sugar-substitute-another-candidate-emerges) Aug. 25, 2015. (Year: 2015).*
KR-1230972-B1 translated doc (Year: 2013).*

(Continued)

*Primary Examiner* — Terry A McKelvey
*Assistant Examiner* — Jacob A Boeckelman
(74) *Attorney, Agent, or Firm* — Morgan, Lewis & Bockius LLP

(57) ABSTRACT

The present application relates to a plant-soaked solution including a saccharide containing allulose and a method of preparing the same.

9 Claims, 3 Drawing Sheets

(56) References Cited

FOREIGN PATENT DOCUMENTS

| | | | |
|---|---|---|---|
| CO | 2019002024 A2 | 3/2019 | |
| EP | 2 090 180 A1 | 8/2009 | |
| EP | 3508073 A1 | 7/2019 | |
| JP | 59187769 A | 10/1984 | |
| JP | 2006008669 A * | 1/2006 | |
| JP | 2013247872 A * | 12/2013 | |
| JP | 2014-138555 A | 7/2014 | |
| JP | 2014-526258 A | 10/2014 | |
| JP | 2016-123285 A | 7/2016 | |
| KR | 100389011 B1 | 6/2003 | |
| KR | 101134542 | 4/2012 | |
| KR | 1230972 B1 * | 2/2013 | |
| KR | 1020150083586 | 7/2015 | |
| KR | 2015-0130324 A | 11/2015 | |
| KR | 2016-0055652 A | 5/2016 | |
| KR | 1020160089551 | 7/2016 | |
| KR | 1020160098249 | 8/2016 | |
| WO | WO-0113727 A1 * | 3/2001 | ............ A01N 37/40 |
| WO | 2015075473 A1 | 5/2015 | |
| WO | 2015/094342 A1 | 6/2015 | |
| WO | 2016/152818 A1 | 8/2016 | |
| WO | 2018/127670 A1 | 7/2018 | |

OTHER PUBLICATIONS

Hisaka Oshima et al., "Decrease in the d-Psicose Content of Processed Foods Fortified with a Rare Sugar", Food Science and Technology Research, 2014, vol. 20, No. 2, pp. 415-421, XP055449504.
Extended European Search Report for corresponding European Patent Application No. 17860618.2 dated Apr. 21, 2020.
https://blog.naver.com/12033566/220733612280, Jun. 11, 2016, [Renewed xylose sucrose from CJ Cheiljedang Beksul Sweetree] Preparing the Prunus mume-sooaked solution with allulose, using xylose sucrose reduced absorption to the body.
PCT/KR2017/006629; PCT International Search Report of the International Searching Authority dated Dec. 4, 2017.
Yuanxia Sun et al., "Antioxidant properties of custard pudding dessert containing rare hexose, d-psicose", Food Control, 2007, 18(3), 220-227.
Hisaka Oshima et al., "Decrease in the d-Psicose Content of Processed Foods Fortified with a Rare Sugar", Food Science and Technology Research, 2014, 20(2), 415-421.
Takahiko Mitani et al., "Phenolics Profile of Mume, Japanese Apricot (*Prunus mume Sieb. et Zucc.*) Fruit", Bioscience, Biotechnology, and Biochemistry, 2013, 77(8), 1623-1627.
Blog by Jin Joo, "Korean Green Plum Extract or Syrup (*Maesil cheong*)", Kimchimari, Authentic Korean Recipes Anyone Can Cook, Jul. 21, 2013.
Zhang Longtao et al., "Progress in Researches on D-psicose , a New Sweetener", Food and Fermentation Industry, vol. 12, No. 34, Dec. 30, 2008, pp. 125-129 (with English abstract on the last page).
Zhirong Gan, "Four Seasons Healthy Fruit and Vegetable Diet Illustration", Sep. 30, 2015, Xinjiang People's Medical Publishing House, p. 208 (together with the English translation of the part cited in the Office Action).
Original and English translation of Office Action Issued for corresponding Chinese National Stage Application No. 201780062651, mailed on Jul. 1, 2022.
Office Action issued for corresponding Colombian National Stage Application No. NC2019/0003424, mailed on Jul. 21, 2022.

* cited by examiner

[FIG. 1]
(a)
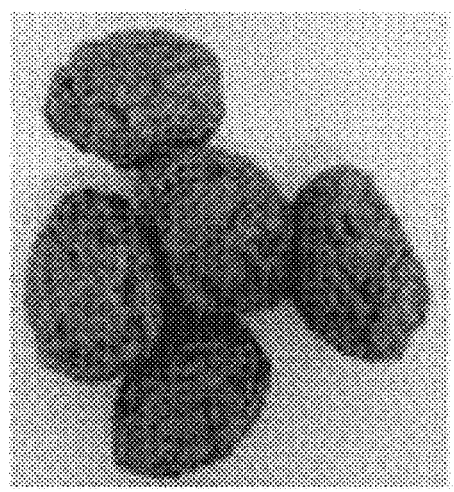
(b)

[FIG. 2]
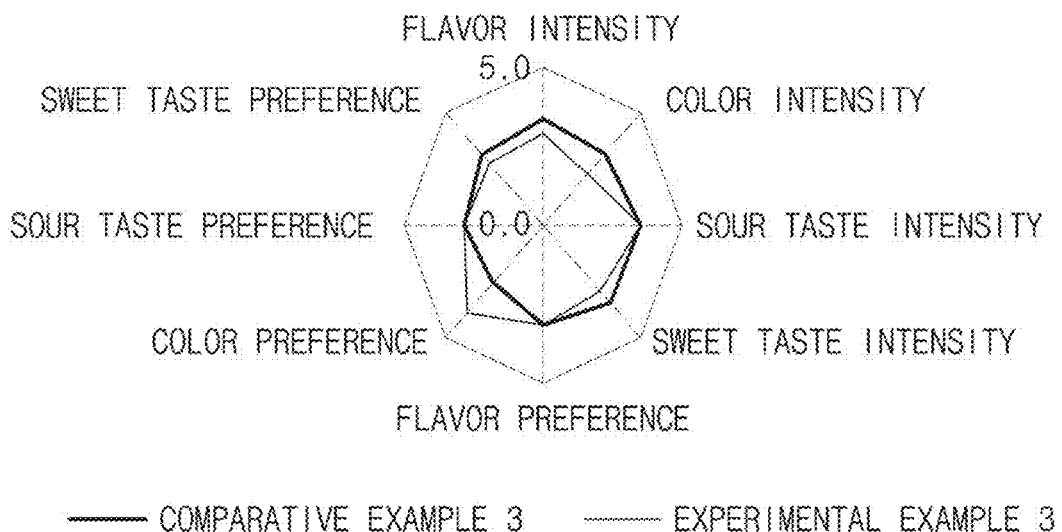
[FIG. 3]
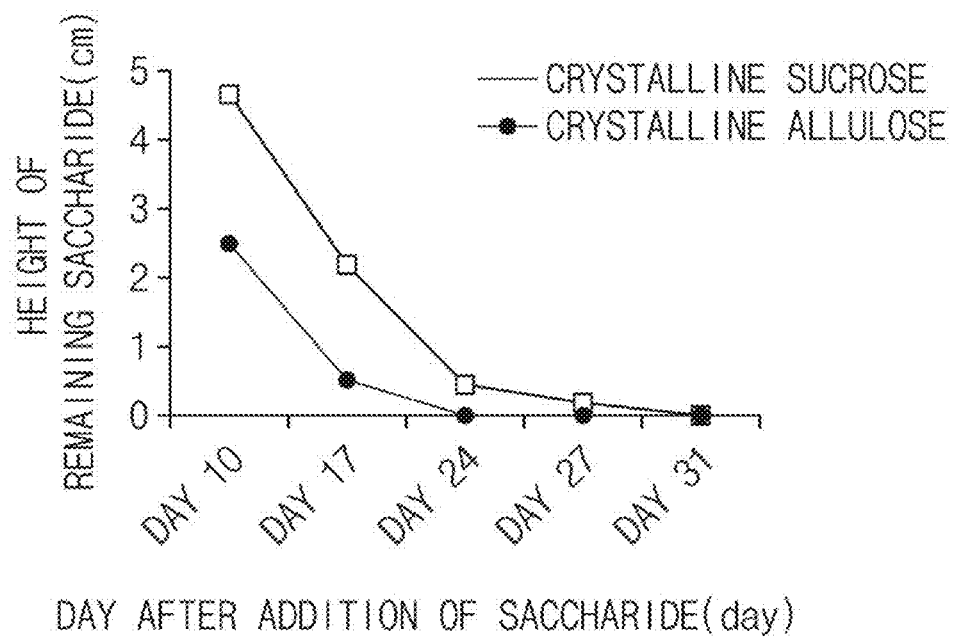

[FIG. 4]

| SOAKING DURATION (DAY) | SOAKING WITH SUCROSE | SOAKING WITH ALLULOSE |
|---|---|---|
| 0 | | |
| 10 | | |
| 17 | | |
| 24 | | |

EXTRACT FROM PLANT STEEPED IN ALLULOSE AND PREPARATION METHOD THEREFOR

TECHNICAL FIELD

The present application relates to a plant-soaked solution containing allulose and a method for preparing the same.

BACKGROUND ART

"Soaked solution" is a food prepared by mixing a raw material for soaking with a saccharide and maintaining soaking for a certain period of time so as to extract a component present in the raw material into the saccharide. The soaked solution is ingested as it is, or diluted and drunk as a drink, or used for a marinade or a sauce.

Conventionally, the saccharide used for the preparation of the soaked solution is sucrose. Since sucrose is present in a solid, it takes a long time to dissolve. In addition, the labor of consumers is needed to mix sucrose and the raw material, which is inconvenient. In addition, there was a disadvantage in that the soaked solution prepared using sucrose contains large amounts of monosaccharaides (such as glucose and fructose) which are produced by decomposing sucrose, and thus, when ingested, blood glucose is rapidly increased and calories are produced.

Allulose (D-psicose), i.e., a C-3 epimer of D-fructose, is a natural saccharide component present in trace amounts in dry grapes, figs and wheat, etc., and has 70% sweetness, compared with sucrose, but has 0 to 0.2 kcal per gram, which is only 0 to 5% of the calories of sucrose (4 kcal/g). For this reason, allulose has attracted attention as the raw material for a sweetener capable of replacing sucrose. However, there has been no report on whether a plant-soaked solution can be prepared using allulose, instead of sucrose.

Under these circumstances, the inventors had attempted to conduct studies for developing a material that can be a substitute for sucrose in the preparation of a plant-soaked solution. As a result, the inventors confirmed that a plant-soaked solution is prepared by extracting a useful component at a level similar to the conventional plant-soaked solution prepared using sucrose when the plant-soaked solution is prepared using allulose. Further, the inventors also found that, when allulose is used in the preparation of the plant-soaked solution, a dissolution rate of allulose is higher than sucrose, and thus the labor accompanying the mixing with the raw material is decreased, and unlike sucrose, it is not decomposed into glucose or fructose, such that the functionality of the allulose itself and low calories can be maintained, thereby completing the present application.

DISCLOSURE OF THE INVENTION

Technical Problem

The present application is directed to providing a plant-soaked solution including a saccharide containing allulose.

The present application is also directed to providing a method for preparing a plant-soaked solution, which includes adding a saccharide containing allulose to a plant.

Hereinafter, the present application is described in more detail. The contents not described in this specification can be sufficiently recognized and inferred by those skilled in the art or similar fields of the present application, and thus, the description thereof will be omitted.

Technical Solution

An aspect of the present application provides a plant-soaked solution including a saccharide containing allulose.

The term "soaked solution" used herein refers to a liquid food prepared by mixing a raw material for soaking with a saccharide and maintaining soaking for a certain period of time so as to extract a component present in the raw material.

According to an exemplary embodiment of the present application, the saccharide containing allulose of the present application may be included at 33 to 67 parts by weight with respect to 100 parts by weight of the plant-soaked solution of the present application. Specifically, the saccharide containing allulose of the present application may be included at 33.3 to 66.7 parts by weight, 44 to 55 parts by weight, 44.4 to 54.5 parts by weight, 48 to 52 parts by weight, or 50 parts by weight with respect to 100 parts by weight of the plant-soaked solution of the present application.

According to another exemplary embodiment of the present application, the allolose of the present application may be contained at 1 to 100 parts by weight with respect to 100 parts by weight of the saccharide containing allulose of the present application based on a dry content. Specifically, the allulose of the present application may be included at 10 to 100 parts by weight, 15 to 100 parts by weight, 30 to 100 parts by weight, 50 to 100 parts by weight, 70 to 100 parts by weight, 90 to 100 parts by weight, 95 to 100 parts by weight, 99 to 100 parts by weight, or 99.5 to 100 parts by weight with respect to 100 parts by weight of the saccharide containing allulose of the present application based on a dry content. The allulose of the present application may be directly extracted from a natural product, or may be prepared by chemical synthesis or a biological method, but the present application is not limited thereto.

According to still another exemplary embodiment of the present application, the saccharide containing allulose of the present application may further include one or more saccharides selected from the group consisting of monosaccharides, disaccharides, oligosaccharides, sugar alcohols, high intensity sweeteners, and liquid saccharides, in addition to allulose.

The term "monosaccharide" used herein refers to the basic unit of a carbohydrate having the simplest structure which cannot be further hydrolyzed by acids, bases or enzymes. Specifically, the monosaccharide of the present application may be arabinose, xylose, fructose, tagatose, allose, glucose or galactose.

The term "disaccharide" used herein refers to a carbohydrate in which two monosaccharides are combined. Specifically, the "disaccharide" of the present application may be sucrose, lactose, maltose, trehalose, turanose, or cellobiose.

The term "oligosaccharide" used herein refers to a carbohydrate in which 3 to 15 monosaccharides are combined. Specifically, the oligosaccharides of the present application may be fructooligosaccharides, isomaltooligosaccharides, xylooligosaccharides, gentiooligosaccharides, maltooligosaccharides, or galactooligosaccharides.

The term "sugar alcohol" used herein refers to a compound in which the carbonyl group of a saccharide is reduced. Specifically, the sugar alcohol of the present application may be erythritol, xylitol, arabitol, mannitol, sorbitol, maltitol, or lactitol.

The term "high intensity sweetener" used herein means a sweetener which is at least 10 times sweeter than sucrose. Specifically, the high intensity sweetener of the present application may be aspartame, acesulfame K, rebaudioside A, or sucralose.

The term "liquid saccharide" used herein refers to a saccharide in the form of a liquid. For example, the liquid saccharide of the present application may include, but is not limited to, starch syrup, honey, maple syrup, agave syrup, and the like.

According to a yet another exemplary embodiment of the present application, the saccharide of the present application may not include sucrose.

The term "plant" used herein refers to a photosynthetic green plant which has a cell wall and uses chlorophyll to be autotroph. The plant of the present application may include parts of the plant (e.g., fruits, leaves, stems, and roots of the plant).

According to yet another embodiment of the present application, the plant of the present application may be a fruit, vegetable, or wild grass.

The term "fruit" used herein refers to a fruit of a woody plant, which can be eaten by a human. Specifically, the fruit of the present application may be one or more fruits selected from the group consisting of Chinese plum (*Prunus mume*), citrus, lemon, citron, grapefruit, lime, quince, Schisandra, bokbunj a, Korean Blackberry (*Rubus coreanus*), pear, apple, grape, mulberry, blueberry, mango, peach, plum (*Prunus salicina*), apricot, sweet persimmon, banana, and jujube. More specifically, the fruit of the present application may be *Prunus mume* or lemon.

The term "vegetable" used herein refers to an herbaceous cultivated plant that can be eaten by a human. Specifically, the vegetable of the present application may be one or more vegetables selected from the group consisting of ginger, onion, red pepper, garlic, radish leaves, balloon flower roots, tomato, strawberry, oriental melon, melon, watermelon, and cucumber.

The term "wild grass" used herein refers to an herbaceous non-cultivated plant that is grown on a mountain or in a field and can be eaten by a human. Specifically, the wild grass of the present application may be one or more wild grasses selected from the group consisting of mugwort, dandelion, plantain, purslane, and arrowroot.

According to yet another exemplary embodiment of the present application, the *Prunus mume*-soaked solution of the present application may further include a polyphenol.

According to yet another exemplary embodiment of the present application, the *Prunus mume*-soaked solution of the present application may be a health functional food for antioxidation.

The plant-soaked solution of the present application may further include food ingredients, for example, vitamins, electrolytes, flavors, colorants, pectic acid and salts thereof, alginic acid and salts thereof, organic acids, protective colloid thickeners, pH adjusters, stabilizers, preservatives, glycerin, carbonating agents, etc., in addition to allulose.

Another aspect of the present application provides a method of preparing a plant-soaked solution, which includes adding a saccharide containing allulose to a plant.

According to an exemplary embodiment of the present application, the saccharide containing allulose of the present application may be added at 50 to 200 parts by weight with respect to 100 parts by weight of the plant of the present application. Specifically, the saccharide containing allulose of the present application may be added at 80 to 120 parts by weight, 90 to 110 parts by weight, 95 to 105 parts by weight or 100 parts by weight with respect to 100 parts by weight of the plant of the present application.

According to another exemplary embodiment of the present application, the saccharide containing allulose of the present application or the allulose may be prepared in a crystalized state.

According to still another exemplary embodiment of the present application, the preparation method of the present application may further include storing a resulting product of the step of adding the saccharide containing allulose to a plant of the present application at a temperature of 0 to 25° C. Specifically, the temperature may be 0 to 20° C., 0 to 15° C., 0 to 10° C., 0 to 5° C., 3 to 25° C., 3 to 20° C., 3 to 15° C., 3 to 10° C., 3 to 5° C., or 4° C. In addition, according to yet another exemplary embodiment of the present application, the storage period of the present application may be 15 days to 6 months, 15 days to 4 month, 1 to 6 months, 1 to 4 months, or 1 to 3 months.

According to yet another exemplary embodiment of the present application, the preparation of the present application may further include, before or after the step of adding a saccharide containing allulose to a plant of the present application, a step of adding one or more saccharides selected from the group consisting of monosaccharides, disaccharides, oligosaccharides, sugar alcohols, high-intensity sweeteners, and liquid saccharides, in addition to allulose.

According to yet another exemplary embodiment of the present application, the preparation method of the present application may further include, after the step of adding a saccharide containing allulose to a plant of the present application, a step of further adding a new plant which is the same as the plant of the present application to the resulting product of the previous step, and then adding a new saccharide which is the same as the saccharide containing allulose of the present application.

According to yet another exemplary embodiment of the present application, the preparation method of the present application may not include a step of adding sucrose, fructose, glucose, or a combination thereof.

Descriptions of the saccharide containing allulose, the allulose, the plant, and the soaked solution, described in the plant-soaked solution, which is an aspect of the present application described above, may be applied equally to the preparation method of the plant-soaked solution of the present application. Therefore, in order to avoid complexity in the specification of the present application, the description of overlapping parts is omitted.

Advantageous Effects

A soaked solution according to the present application can include a useful component at the same level as that of the conventional soaked solution prepared using sucrose, and since allulose is not decomposed into glucose or fructose, the functionality of the allulose itself and low calories can be maintained. Therefore, the soaked solution of the present application can replace the conventional soaked solution prepared using sucrose.

In addition, when the soaked solution is prepared using allulose, the dissolution rate of the allulose is higher than that of sucrose, consumer labor accompanying the mixing of the raw material and the saccharide can be reduced.

BRIEF DESCRIPTION OF THE DRAWINGS

FIG. 1 is a set of photographs of tissues of *Prunus mume* soaked; FIG. 1A shows the tissue of *Prunus mume* steeped in sucrose for 3 months, and FIG. 1B shows the tissue of *Prunus mume* steeped in allulose for 3 months.

FIG. 2 is a spider map of sensory evaluation for Comparative Example 3 and Experimental Example 3 of exemplary embodiments of the present application.

FIG. 3 is a graph comparing the dissolution rates of sucrose and allulose during soaking.

FIG. 4 is a set of images comparing the dissolution rates of sucrose and allulose during soaking.

MODES FOR CARRYING OUT THE INVENTION

Although the present application will be described in detail with reference to the following Examples, the following examples are provided by way of illustration, and the present application is not limited thereto.

PREPARATION EXAMPLE 1

Preparation of *Prunus mume*-Soaked Solutions using Allulose

Domestic *Prunus mume* fruit (green plum) was cleanly washed with distilled water and allowed to dry naturally for one day. Then, stems were removed, and the fruit was heated in hot water with a temperature of 100° C. for 10 minutes, and then 0.95 kg of the resulting fruit was put into a naturally-dried container (glass, capacity of 5 kg). Afterward, 0.95 kg of allulose (crystalline, purity of 99% or more, C J Cheilj edang), the same amount of the *Prunus mume* and the same amount of allulose were sequentially added one more time. Subsequently, the resulting product was maintained under cold and dark conditions (4° C., light-blocked condition, Korean Food Code) for 1, 2 or 3 months, and then filtered with a sieve (8 mesh). The filtrate was collected, thereby preparing *Prunus mume*-soaked solutions [Experimental Example 1 (maintenance for 1 month), Experimental Example 2 (maintenance for 2 months) and Experimental Example 3 (maintenance for 3 months)].

PREPARATION EXAMPLE 2

Preparation of Lemon-Soaked Solution using Allulose

Lemon was washed with baking soda, washed with distilled water to remove a pesticide residue from the surface of the lemon, and naturally dried for one day. The lemon was sliced to a thickness of 0.5 to 2 cm, and then seeds were removed. By the same method as described in Preparation Example 1, 400 g of the lemon slices were put into a container (glass, capacity: 1 kg), 400 g of allulose was added thereto, and then the same amount of lemon slices and the same amount of allulose were sequentially added one more time. Subsequently, the resulting product was maintained under cold and dark conditions (4° C., light-blocked condition, Korean Food Code) for 15 days, and then filtered with a sieve (8 mesh). The filtrate was collected, thereby preparing a lemon-soaked solution (Experimental Example 4).

PREPARATION EXAMPLE 3

Preparation of *Prunus mume*-Soaked Solutions and Lemon-Soaked Solution using Sucrose

*Prunus mume*-soaked solutions [Comparative Example 1 (maintenance for 1 month), Comparative Example 2 (maintenance for 2 months), and Comparative Example 3 (maintenance for 3 months)] and a lemon-soaked solution were prepared in the same manner as described in Preparation Examples 1 and 2 only by replacing allulose with sucrose (crystalline white sucrose, C J CheilJedang).

EXAMPLE 1

Evaluation of *Prunus mume*-Soaked Solutions 1-1. Evaluation of Tissue Change

In the production of the *Prunus mume*-soaked solution, the moisture in the raw material of *Prunus mume* was drained from the inside of the tissue to outside thereof due to osmosis, thereby shrinking the tissue. Therefore, it is usually judged that the more tissue of soaked *Prunus mume* contracts, the further the soaking progresses. Thus, changes in *Prunus mume* tissues after 3 months from the start of soaking in Preparation example 1 and Preparation example 3 were visually observed.

As a result, it was confirmed that tissue of the soaked *Prunus mume* of Preparation Example 1 (FIG. 1B) contracted at the same level of the soaked *Prunus mume* of Preparation Example 3 (FIG. 1A) (FIG. 1).

1-2. Evaluation of Physical Properties (Solid Content, pH and Color Value) of Soaked Solution In order to verify whether the soaking was carried out in the preparation of a *Prunus mume*-soaked solution using allulose at the same level as in the *Prunus mume*-soaked solution using sucrose, physical properties (solid content, pH and color value) of Comparative Examples 1, 2 and 3 and Experimental Examples 1, 2 and 3 were measured and compared.

Specifically, the solid content (g content of solid content dissolved in 100 g of soaked solution) was measured using a refractometer (ATAGO, Automatic Digital Refractometer RX-5000α), and the pH was measured using a digital pH meter (METTLER TOLEDO, SEVEN COMPACT with InLab® Viscous Pro pH). 5 g of each soaked solution as a sample was put into a beaker, and then diluted using the following proportional expression of Expression 1, thereby preparing an aqueous solution diluted to 30 Brix % (hereinafter, a diluted sample). After a 1-cm cell was filled with the diluted sample, absorbance was measured at a wavelength of 420 nm using a spectrophotometer (HITACHI, Double Beam Spectrophotometer U-2900), and the color value of each sample was calculated according to the following Expression 2.

Proportional Expression: Brix % of sample ×weight of sample=Brix % of diluted sample×(weight of sample+weight of distilled water)   [Expression 1]

Color value (IU)=$A \times B / C \times D$   [Expression 2]

*$A$: Absorbance (nm) at 420 nm, $B$: Conversion factor 1000 to IU value, $C$: Length (cm) of sample cell, $D$: Sampling amount (g/mL)=(Brix %/100)×specific gravity Statistical analysis was performed using the SAS 9.1 program (SAS Inc., Cary, NC, USA), and the results were analyzed using a Student's t-test. All analyses were tested for significance at $p<0.05$.

As a result, there were no significant changes in solid content and pH in Experimental Examples and Comparative Examples, but the color values in Experimental Examples were significantly lower than those of Comparative Examples (Table 1). Therefore, when the *Prunus mume*-soaked solution was prepared using allulose, the solution had the same levels of solid content and pH as that using sucrose, and had a lower color value than that using sucrose, showing that the color preference of Experimental Example 3 is better than that of Comparative Example 3.

TABLE 1

| | Solid content (Brix %) | | | pH | | | Color value (IU) | |
|---|---|---|---|---|---|---|---|---|
| Comparative Example 1 | Comparative Example 2 | Comparative Example 3 | Comparative Example 1 | Comparative Example 2 | Comparative Example 3 | Comparative Example 1 | Comparative Example 2 | Comparative Example 3 |
| 57.75 | 56.15 | 54.87 | 3.12 | 3.21 | 3.34 | 130 | 1579 | 2331 |
| Experimental Example 1 | Experimental Example 2 | Experimental Example 3 | Experimental Example 1 | Experimental Example 2 | Experimental Example 3 | Experimental Example 1 | Experimental Example 2 | Experimental Example 3 |
| 53.69 | 53.09 | 53.04 | 3.14 | 3.21 | 3.28 | 74 | 86 | 163 |

1-3. Confirmation of Citric Acid Content in Soaked Solution

In order to verify whether the soaking is carried out at the same level as for the *Prunus mume*-soaked solution using sucrose to extract useful components in the preparation of the *Prunus mume*-soaked solution using allulose, a content of citric acid, which is one of the major useful components of *Prunus mume*, in the *Prunus mume*-soaked solution was measured by High Performance Liquid Chromatography (HPLC).

A test solution was prepared by inputting 1 g of one sample of Experimental Example 1, 2 and 3, and Comparative Example 1, 2 and 3 into a 50 mL volumetric flask, dissolving the sample in distilled water to adjust the solution to a volume of 50 mL (20 g/L), and then filtering the resulting solution through a 0.2 µm filter. A standard solution was prepared by inputting 0.5 g of citric acid monohydrate (Sigma Aldrich) into a 50 mL volumetric flask, dissolving the citric acid monohydrate in distilled water to adjust the solution to a volume of 50 mL (10 g/L), diluting the solution to concentrations of about 0.3125 g/L, 0.625 g/L, 1.25 g/L, 2.5 g/L, 5 g/L and 10 g/L, and filtering the diluted solution through a 0.2 µm filter.

The prepared test solution and standard solution were analyzed by HPLC (Alliance, Waters, e2695 Separation Modules, USA/Waters Column Heater Module/RI detector Water 2414/Empower™ Software) under the conditions listed in Table 2 below.

TABLE 2

| | |
|---|---|
| Mobile phase | 5 mM $H_2SO_4$ |
| Column | 300 mm × 7.8 mm Amninex 87H (Bio Rad) |
| Flow rate | 0.6 mL/min |
| Temperature | 35° C. |
| Input volume | 20 µL |
| Detector | Diode Array Detector (DAD) |

After HPLC analysis, a calibration curve was obtained with the citric acid content (g/L) as the abscissa axis, and an area of the chromatogram as the ordinate axis, and the citric acid area of each of Experimental Examples 1, 2 and 3 and Comparative Examples 1, 2 and 3 was read, and then the citric acid content was calculated from the calibration curve using Expression 3 below.

$$\text{Citric acid content}(g/100\ g\ \text{of soaked solution}) = \frac{\text{Concentration of obtained from calibration curve (g/L)} \times \text{Diluted volume(mL)} \times 100}{\text{Sampling amount (g)} \times 1000}$$ [Expression 3]

As a result, it was confirmed that there is no significant difference in citric acid content between Experimental Examples 1, 2 and 3 and Comparative Examples 1, 2 and 3 (Table 3). Therefore, it can be confirmed that, when the soaked solution was prepared using allulose, the solution with the same level of the useful component as when using sucrose was prepared.

TABLE 3

| Citric acid content (g/100 g of soaked solution) | | |
|---|---|---|
| Comparative Example 1 | Comparative Example 2 | Comparative Example 3 |
| 2.0 | 2.1 | 2.9 |
| Experimental Example 1 | Experimental Example 2 | Experimental Example 3 |
| 1.9 | 2.0 | 2.7 |

1-4. Organoleptic Evaluation

Samples of Experimental Example 3 and Comparative Example 3 were diluted in lukewarm water at a ratio of 1:3, and each diluted sample was subjected to organoleptic analysis by 10 trained panelists to evaluate four intensity attributes (flavor/color/sour taste/sweet taste) and preference attributes (flavor/color/sour taste/sweet taste/overall preference).

Glossary of Organoleptic Evaluation

1) Flavor intensity/preference: the intensity/personal preference of a flavor of the soaked solution 2) Color intensity/preference: the intensity/personal preference of the lightness and thickness of the color of the soaked solution 3) Sour taste intensity/preference: the intensity/personal preference of a sour taste 4) Sweet taste intensity/preference: the intensity/personal preference of a sweet taste from the saccharide 5) Overall preference: overall personal preference As a result, as shown in Example 1-2, it was confirmed that Experimental Example 3 has a significantly lower color intensity than Comparative Example 3, but has a significantly higher color preference. It is determined that this is because Experimental Example 3 is clearer and more transparent than Comparative Example 3. It was confirmed that Experimental Example 3 exhibits similar organoleptic attributes, specifically, intensity and preference attributes, to Comparative Example 3 (Table 4 and FIG. 2).

TABLE 4

| 5-point scale | Comparative Example 3 | Experimental Example 3 | p-value |
|---|---|---|---|
| Flavor intensity | 3.4 | 2.9 | 0.09 |
| Color intensity | 3.2 | 2.2 | 0.02* |
| Sour taste intensity | 3.5 | 3.5 | 0.90 |
| Sweet taste intensity | 3.4 | 2.9 | 0.14 |
| Flavor preference | 3.2 | 3.1 | 0.75 |
| Color preference | 2.5 | 3.9 | 0.00* |
| Sour taste preference | 2.9 | 2.9 | 1.00 |
| Sweet taste preference | 3.1 | 2.8 | 0.27 |
| Overall preference | 3.2 | 3.1 | 0.72 |

*$p < 0.05$ 1-5. Confirmation of Dissolution Rates of Sugar and Allulose used in Soaked Solutions Dissolution rates were observed by measuring heights of the remaining saccharide by elapsed days after the addition of sucrose and allulose to *Prunus mume* in Preparation Example 1 and Preparation Example 3. Stirring was performed 20 times at intervals of 3 days immediately after the addition of each of sucrose and allulose. The resulting solutions were allowed to stand for 6 hours, and then a height of the remaining saccharide (cm) was measured using a ruler (FIGS. 3 and 4).

As a result, it was confirmed that sucrose crystals were completely dissolved on day 31 after addition, but allulose crystals were completely dissolved on day 24 after addition. It was confirmed that, when the soaked solution was prepared using allulose, compared with when using sucrose, the convenience of use is increased due to a high dissolution rate of crystals.

1-6. Confirmation of Allulose Dissolution

In order to verify whether the calorie reduction effect and functionality of allulose were maintained in the soaked solution prepared using allulose, it was confirmed whether allulose used in the preparation of the soaked solution was decomposed or not.

Specifically, the contents of allulose and free saccharides (sucrose, glucose and fructose) in Experimental Examples 1, 2 and 3 and Comparative Examples 1, 2 and 3 were measured using HPLC. A test solution was prepared by inputting 1 g of each sample of Experimental Example 1, 2 and 3 and Comparative Example 1, 2 and 3 into a 50 mL volumetric flask, dissolving the sample in distilled water to adjust the solution to a volume of 50 mL (20 g/L), and filtering the solution through a 0.2 μm filter. A standard solution was prepared by inputting 1 g of a standard product of sucrose (SigmaS7903, CAS No. 57-50-1), glucose (SigmaG7528, CAS No. 50-99-7), fructose (SigmaF0127, CAS No. 57-48-7) or allulose (SigmaP8043, CAS No. 551-68-8) into a 50 mL volumetric flask, dissolving the same in distilled water, diluting the resulting solution to a concentration of, for example, about 0.625 g/L, 1.25 g/L, 2.5 g/L, 5 g/L, 10 g/L or 20 g/L, and filtering the diluted solution through a 0.2 μm filter.

The prepared test solutions and standard solutions were analyzed using HPLC (Alliance, Waters, e2695 Separation Modules, USA/Waters Column Heater Module/RI detector Water 2414/Empower™ Software) under the conditions listed in Table 5 below.

TABLE 5

| | |
|---|---|
| Mobile phase | Distilled water (HPLC Grade) |
| Column | 7.8 mm × 300 mm Aminex HPX87C (Bio Rad) |
| Flow rate | 0.6 mL/min |
| Temperature | 80° C. |
| Input volume | 20 μL |
| Detector | refractive index detector (RID) |

After HPLC analysis, a calibration curve was obtained with the contents (g/L) of allulose and free sugars (sucrose, glucose and fructose) as the abscissa axis, and the area of the chromatogram as the ordinate axis, and the allulose and free sugar areas of each of Experimental Examples 1, 2 and 3 and Comparative Examples 1, 2 and 3 were read, and the allulose and free sugar contents were calculated from the calibration curve using Expressions 4 and 5 below.

$$\text{Allulose content(g/100 g of soaked solution)} = \frac{\text{Concentration of obtained from calibration curve (g/L)} \times \text{Diluted volume(mL)} \times 100}{\text{Sampling amount (g)} \times 1000} \quad \text{[Expression 4]}$$

$$\text{Free sugar content(g/100 g of soaked solution)} = \frac{\text{Concentration of obtained from calibration curve (g/L)} \times \text{Diluted volume(mL)} \times 100}{\text{Sampling amount (g)} \times 1000} \quad \text{[Expression 5]}$$

As a result, in Comparative Example 3, it was confirmed that only 16.1 g of sucrose remains, and about 56% of the added sucrose is decomposed into glucose and fructose, whereas in Experimental Example 3, allulose remains as is without decomposition (Table 6). Therefore, in the soaked solution prepared using sucrose, calories are generated due to sucrose, glucose and fructose included therein, and a rapid increase in blood glucose may occur when ingested, but in the soaked solution using allulose, allulose is not decomposed, suggesting that a calorie reduction effect is exhibited, compared with the conventional soaked solution.

TABLE 6

| Sucrose content | | | Glucose content | | | Fructose content | | | Allulose content | | |
|---|---|---|---|---|---|---|---|---|---|---|---|
| Comparative Example 1 | Comparative Example 2 | Comparative Example 3 | Comparative Example 1 | Comparative Example 2 | Comparative Example 3 | Comparative Example 1 | Comparative Example 2 | Comparative Example 3 | Comparative Example 1 | Comparative Example 2 | Comparative Example 3 |
| 42.5 | 23.7 | 16.1 | 8.9 | 11.8 | 14.8 | 4.2 | 4.7 | 5.5 | — | — | — |
| Experimental Example 1 | Experimental Example 2 | Experimental Example 3 | Experimental Example 1 | Experimental Example 2 | Experimental Example 3 | Experimental Example 1 | Experimental Example 2 | Experimental Example 3 | Experimental Example 1 | Experimental Example 2 | Experimental Example 3 |
| — | — | — | — | — | — | — | — | — | 53.7 | 53.6 | 53.6 |

(Unit: g/100 g of soaked solution)

1-7. Confirmation of Total Polyphenol Content in Soaked Solution

To verify the functionality of the *Prunus mume*-soaked solution, a polyphenol content in the soaked solution was measured using a microplate reader (Powerwave XS, BioTek, USA).

A 2% sodium carbonate reagent was prepared by inputting 2 g of sodium carbonate (Sigma223484, CAS No. 497-19-8) into a 100 mL volumetric flask, and adding distilled water to adjust the solution to a volume of 100 mL. A 50% Folin-Ciocalteu's phenol reagent was prepared by mixing the Folin-Ciocalteu's phenol reagent (SigmaF9252-1 L) and distilled water at 1:1, and then covered with an aluminum foil to prevent light transmission.

To prepare a test solution, the soaked solution of Experimental Example 3 or Comparative Example 3 was diluted with distilled water at 1:1, 0.1 mL of the diluted solution was mixed with 0.1 mL of the 50% Folin-Ciocalteu's phenol reagent and 2 mL of the 2% sodium carbonate, the mixture was maintained in a dark room for 30 minutes, and absorbance was measured at 750 nm.

A standard solution was prepared by inputting 0.4 g of gallic acid (SigmaG7384, CAS No. 149-91-7) into a 100 mL volumetric flask, adding distilled water to adjust the solution to a volume of 100 mL, and diluting the resulting solution to a concentration of 31.25 ppm, 62.5 ppm, 125 ppm, 250 ppm or 500 ppm. After mixing the reagents as in the method used for the standard solution, the test solution was maintained in a dark place for 30 minutes, and absorbance at 750 nm was measured.

After the measurement of absorbance, a calibration curve was obtained with the absorbance of the standard solution as the abscissa axis, and the concentration of the standard solution as the ordinate axis, and a total polyphenol content of each of Experimental Example 3 and Comparative Example 3 was calculated using Expression 6 below.

Total polyphenol content (mg/mL)=$(A \times B \times C)/D$ [Expression 6]

*A: Total volume of test solution (mL), B: Dilution factor, C: Total polyphenol concentration in test solution (mg/mL), D: Sampling volume (mL)

As a result, it was confirmed that, in Experimental Example 3, the total polyphenol content is significantly higher than that in Comparative Example 3 (Table 7). Therefore, it was confirmed that when the *Prunus mume*-soaked solution is prepared using allulose, the solution with a higher total polyphenol content than when using sucrose can be prepared.

TABLE 7

| Classification | Comparative Example 3 | Experimental Example 3 | p-value |
|---|---|---|---|
| Total polyphenol (mg/mL) | 7.8 | 14.3 | 0.00* |

*p < 0.05

1-8. Confirmation of Antioxidant Efficacy of Soaked Solution

To verify the antioxidant efficacy of the *Prunus mume*-soaked solution prepared using allulose, the scavenging activity of a free radical 1,1-diphenyl-2-picrylhydrazyl (DPPH) was measured using a microplate reader (Powerwave XS, BioTek, USA).

A 100 µM DPPH reagent was prepared by precisely measuring 3.9432 mg of a DPPH reagent and adjusting the reagent to a volume of 100 mL with ethanol (99.5%, Daejung Chemicals and Metals, CAS No. 64-17-5).

1 mL of the 100 µM DPPH reagent was added to each of 0.2 mL of Experimental Example 3 and 0.2 mL of Comparative Example 3, and the solution was maintained in a dark place for 15 minutes, and then absorbance was measured at 517 nm. The antioxidant efficiency of Experimental Example 3 and Comparative Example 3 was calculated using Expression 7 below.

$$DPPH(\%) = 1 - \left(\frac{\text{Absorbance of sample}}{\text{Absorbance of control}}\right) \times 100 \quad \text{[Expression 7]}$$

As a result, it was confirmed that the DPPH value of Experimental Example 3 is significantly higher than that of Comparative Example 3 (Table 8). Therefore, it can be seen that when the *Prunus mume*-soaked solution was prepared using allulose, the solution had very high antioxidant efficiency.

TABLE 8

| Classification | Comparative Example 3 | Experimental Example 3 | p-value |
|---|---|---|---|
| DPPH (%) | 20.5 | 85.0 | 0.00* |

*p < 0.05

EXAMPLE 2

Evaluation of Lemon-Soaked Solution 2-1. Evaluation of Physical Properties of Soaked Solution (Solid Content, pH and Color Value)

In order to verify whether the soaking was carried out in the preparation of a lemon-soaked solution using allulose at the same level as in a lemon-soaked solution using sucrose, physical properties (solid content, pH and color value) of the soaked-solutions of Comparative Example 4 and Experimental Example 4 were measured and compared. Methods of measuring a solid content, pH and a color value are the same as described in Example 1-2.

As a result, the solid content was 50 Brix % or more, which is the same as that of the conventional soaked solution, and there was no significant difference in pH from the lemon-soaked solution prepared using sucrose. The color value was significantly lower than that of the conventional soaked solution, showing that color preference was excellent (Table 9). Therefore, when the lemon-soaked solution was prepared using allulose, it was confirmed that the solution had almost the same levels of physical properties as the lemon-soaked solution prepared using sucrose.

TABLE 9

| Classification | Solid content (Brix %) | pH | Color value (IU) |
|---|---|---|---|
| Comparative Example 4 | 59.51 | 3.38 | 2231 |
| Experimental Example 4 | 55.64 | 3.36 | 1842 |

2-2. Confirmation of Allulose Decomposition

In order to verify whether the low calories and functionality of allulose were maintained in the lemon-soaked solution using allulose, it was confirmed whether allulose used in the preparation of the lemon-soaked solution was decomposed or not.

Specifically, the contents of allulose and free saccharides (sucrose, glucose and fructose) in Experimental Example 4 and Comparative Example 4 were measured using HPLC, and measurement methods and HPLC analysis conditions were the same as described in Example 1-6.

As a result, it can be confirmed that, in Comparative Example 4, sucrose was decomposed into glucose and fructose, whereas allulose used in the preparation of Experimental Example 4 was not decomposed but remained as is (Table 10). Therefore, it was confirmed that allulose in the lemon-soaked solution was not decomposed like in the *Prunus mume*-soaked solution, and thus the calorie reduction effect and functionality of allulose can be maintained as is.

TABLE 10

| Classification | Sucrose content | Glucose content | Fructose content | Allulose content |
|---|---|---|---|---|
| Comparative Example 4 | 49.4 | 3.6 | 3.1 | — |
| Experimental Example 4 | — | — | — | 56.2 |

(Unit: g/100 g of soaked solution)

2-3. Confirmation of Vitamin C Content in Soaked Solution

In order to verify whether the soaking is carried out at the same level as in the lemon-soaked solution using sucrose and the useful components are extracted when allulose is used for preparation of lemon-soaked solution, the content of vitamin C, which is one of main useful components of lemon, in the lemon-soaked solution was measured by high performance liquid chromatography (HPLC).

A test solution was prepared by inputting 1 g of each sample of Experimental Example 4 and Comparative Example 4 into a 50 mL volumetric flask, dissolving the sample in distilled water to adjust the solution to a volume of 50 mL (20 g/L), and then filtering the resulting solution through a 0.2 μm filter. A standard solution was prepared by inputting 0.001 g of a vitamin C standard product (L-Ascorbic acid, SigmaA5960, CAS No. 50-81-7) into a 10 mL volumetric flask, dissolving the vitamin C in distilled water to adjust the solution to a volume of 10 mL (0.1 g/L), diluting the solution to a concentration, for example, about 0.00625 g/L, 0.0125 g/L, 0.025 g/L, 0.05 g/L or 0.1 g/L, and filtering the diluted solution through a 0.2 μm filter. The prepared test solutions and standard solutions were analyzed by HPLC (Alliance, Waters, e2695 Separation Modules, USA/Waters Column Heater Module/RI detector Water 2414/Empower™ Software) under analysis conditions listed in Table 11 below.

TABLE 11

| | |
|---|---|
| Mobile phase | Acetonitrile 90% + formic acid 10% |
| Column | 250 mm × 4.6 mm Intersil ® HPLC |
| Flow rate | 0.7 mL/min |
| Temperature | 35° C. |
| Input volume | 10 μL |
| Detector | diode array detector (DAD) |

After HPLC analysis, a calibration curve was obtained with the citric acid content (g/L) as the abscissa axis and an area of the chromatogram as the ordinate axis, and the vitamin C areas in the test solutions of Experimental Example 4 and Comparative Example 4 were read and then the vitamin C contents were calculated from the calibration curve using Expression 8 below.

$$\text{Vitamin } C \text{ content}(g/100 \text{ g of soaked solution}) = \frac{\text{Concentration of obtained from calibration curve } (g/L) \times \text{Diluted volume}(mL) \times 100}{\text{Sampling amount } (g) \times 1000}$$
[Expression 8]

As a result, it was confirmed that there is no significant difference in vitamin C content between Experimental Example 4 and Comparative Example 4 (Table 12). Therefore, it was confirmed that, when the lemon-soaked solution was prepared using allulose, the solution with the same level of the useful component as when using sucrose was prepared.

TABLE 12

| Classification | Vitamin C (mg/100 g of soaked solution) |
|---|---|
| Comparative Example 4 | 30.5 |
| Experimental Example 4 | 28.3 |

The invention claimed is:

1. A plant-soaked solution composition comprising a plant and a saccharide containing allulose, wherein the plant-soaked solution composition is obtained by:
   mixing the plant with saccharide containing allulose; and
   soaking the plant with the saccharide containing allulose for 15 days to 6 months to provide the plant-soaked solution composition,
   wherein the ratio of the saccharide containing allulose: plant-soaked solution is 33 to 67 parts by weight: 100 parts by weight of the soaked solution,
   wherein the allulose is present in an amount of 1 to 100 parts by weight: 100 parts by weight of the saccharide containing allulose, based on dry content, and
   wherein the plant comprises fruit.

2. The plant-soaked solution composition of claim 1, wherein the saccharide does not comprise sucrose.

3. The plant-soaked solution composition of claim 1, wherein the fruit comprises lemon.

4. The plant-soaked solution composition of claim 3, which is a health functional food for antioxidation.

5. The plant-soaked solution composition of claim 1, wherein the fruit comprises plum.

6. The plant-soaked solution composition of claim 1, wherein the fruit comprises one or more fruits selected from the group consisting of *Prunus mume*, citrus, lemon, citron, grapefruit, lime, quince, schizandra, *rubus coreanus*, pear, apple, grape, mulberry, blueberry, mango, peach, *Prunus salicina*, apricot, sweet persimmon, banana, and jujube.

7. A method of preparing a plant-soaked solution, comprising
   Preparing the plant-soaked solution composition of claim 1,
   filtering the plant-soaked solution composition, and
   collecting the filtered solution, wherein the filtered solution is the plant-soaked solution.

8. The method of claim 7, wherein the plant-soaked solution further comprises polyphenol and the content of total polyphenol in the plant-soaked solution is 14.3 mg/ml or more.

9. A method of extracting polyphenol from fruit in the plant-soaked solution composition of claim 1, comprising adding saccharide containing allulose to the plant.

* * * * *